United States Patent [19]

Hrebenink

[11] Plant 4,219

[45] Mar. 7, 1978

[54] POINSETTIA PLANT

[75] Inventor: Alexander Hrebenink, Perkasie, Pa.

[73] Assignee: Mikkelsens, Inc., Ashtabula, Ohio

[21] Appl. No.: 780,983

[22] Filed: Mar. 24, 1977

[51] Int. Cl.[2] ..... A01H 5/00
[52] U.S. Cl. ..... Plt./86
[58] Field of Search ..... Plt./86

*Primary Examiner*—Robert E. Bagwill
*Attorney, Agent, or Firm*—Donald D. Jeffery

EXEMPLARY CLAIM

A poinsettia plant having upright growth with vigorous self branching in all seasons, from the base to the terminal tip of the plant. There is complete flowering of each shoot, and uniform flowering response from bottom to top. The cultivar has excellent keeping qualities, cream white bract color, and fast and uniform rooting from an abundance of cuttings from each plant. The self branching is initiated at fully developed nodes 4"–5" above the soil line in 4" pots, with 6 to 8 mature leaves, and this is believed to be an unique characteristic.

1 Drawing Figure

The present invention relates to a new and distinctive white cultivar of poinsettia plant known by my identification number 75-H-HI, and botanically known as *Euphorbia pulcherrima.*

The new cultivar is the result of a controlled cross of my previously patented cultivar Wonder Star, U.S. Plant Pat. No. 3,917, and my white seedling of Eckespoint C-1, a well known commercial cultivar. The new cultivar has been asexually reproduced by cuttings in my greenhouses at Perkasie, Pa. and has been found to retain its distinctive characteristics through successive propagations.

The following characteristics distinguish the new cultivar from its parent and from other poinsettias commercially known and used in the floriculture industry:

1. The most obvious and outstanding characteristic of my new cultivar is the dominant self branching from the base to the terminal tip of the plant and the complete flowering of each shoot from bottom to the top. In previously discovered self branching plants, namely Annette Hegg, U.S. Plant Pat. No. 2,962, MIKKEL Scandia, U.S. Plant Pat. No. 3,122, and my cultivar Wonder Star, above referred to, the self branching occurs only in the lower extremities of the plants of these cultivars. Furthermore, in the above three cultivars it is generally observed that self branching only occurs during periods of high light. In my new cultivar, however, the self branching occurs in all seasons.

2. As illustrated in the colored photographic drawing, flowering is quite uniform in response from bottom to top. The economic potential of such a characteristic should be quite valuable for pinched plants, hanging baskets, and the development of tree type decorative pot plants by the removal of lower leaves.

3. Although not tested at this time, there is tremendous potential in the new cultivar for further breeding purposes.

4. The keeping qualities of the new cultivar are comparable to present day, long lasting commercial white cultivars such as MIKKEL White Rochford and Annette Hegg White.

5. Self branching occurs at every node. Although the lateral shoots arising at each node may be somewhat thin, propagators could crop large numbers of cuttings from a relatively few number of stock plants, a valuable economic factor. Rooting is fast, uniform, and plentiful on all cuttings regardless of the location on the plant.

6. Although the center of the bract head is somewhat open, this does not distract from the overall value of my new cultivar. The cyathias hold quite long, the bracts are full, remain flat and horizontal and seem very resistant to discoloring of their edges by botrytis. There were 22 flowering shoots on the nonpinched plant in the accompanying photograph.

7. Small vegetative plants 4"–5" above the soil line grown in 4" styrofoam pots in mid winter had self branching initiated at fully developed nodes, numbering six to eight mature leaves; the length of these laterals varied from 1" at the lower nodes to ¼" at the uppermost node. Such phenomenon has not been reported before.

8. From the nature of the growth of this cultivar it is conceivable that with proper cultural techniques an entirely new type and set of poinsettia plant forms could be introduced to the public.

9. The rate of top growth declines as the number and growth of lateral shoots increases. Removal of side growth speeds up top growth.

10. Removal of lower foliage at maturity allows the side shoots to develop higher quality bracts. Early removal of primary foliage allows greater growth of lateral shoot foliage.

The accompanying colored photographic drawing illustrates the overall appearance of the new cultivar, with the colors being as true as possible to obtain in color reproduction of this type.

The following is a detailed description of the new cultivar based on plants produced under commercial practices in my greenhouses at Perkasie, Pa. Color references are to the Royal Horticultural Society Colour Chart except where general color terms are used.

Parentage: Wonder Star crossed with a white seedling of Eckespoint C-1.

Form of plant: Upright with vigorous self branching.

Growth habit: Initially from cuttings, top growth is quite rapid but declines as the number of side shoots initiate and develop.

Rooting: Rooting is rapid in 10–12 days, uniform, dendritic, abundant.

Blooming habit: Flowering would be considered early, with approximately a nine week response at 65° F in October/November. Flowering is uniform on all shoots.

Blooming season: Late November. Flowering can be induced throughout the year by commercial forcing techniques of regulating the influencing factors of the environment.

Foliage:

*Size.*—Generally small to moderate, being 2"-3" wide by 3"-4" long, with petioles up to 2" long as illustrated.

Quantity: Average for poinsettias.

Color:

*New foliage.*—Upper side — yellow green 146A; under side — yellow green 147B-C.

*Old Foliage.*—Upper side — darker than yellow green 147A; under side — near yellow green 147B.

Shape: Generally ovate to oval.

Texture:

*Upper side.*—Veins recessed, glabrous.

*Under side.*—Veins strongly protruding.

*Venation.*—Pinnate.

Edge or margin: From slightly sinuate to entire.

Aspect: Petioles nearly horizontal with older blades hanging downward.

Disease resistance: No diseases noted on foliage or bracts, no root rot problems recorded to date.

Flowers (cyathia):

*Borne.*—At various angles to the main flowering stems but eventually turning up; usually three main flowering stems with laterals developing in later stages.

*Quantity.*—Average to above average for poinsettias, comparable to MIKKEL White Rochford.

*Continuity.*—Flowering has been observed from natural flowering of late November into March. Cyathias do not develop on laterals if crowded by other plants or the leaf canopy.

Bracts: Slightly cream white bracts, the primary bracts being the shape and size of leaves and the secondary bracts being oblong with noticeable twisting of the apice; the bracts are from 1" to 2" wide by up to 5" long, with the bracts of the lateral shoots being proportionately smaller.

*Color.*—Top — Cream white; under — Generally near white.

Reproductive organs:

*Stamens.*—Color, light green to translucent green.

*Pollen.*—Color, yellow.

*Styles.*—Color, very light green to colorless.

*Ovaries.*—Color, when mature green 146A-147B.

I claim:

1. A new and distinct cultivar of poinsettia plant characterized particularly as to novelty by the combined characteristics of upright growth with vigorous self branching in all seasons, from the base to the terminal tip of the plant, and the complete flowering of each shoot; uniform flowering response from bottom to top; excellent keeping qualities; cream white bract color; fast and uniform rooting from an abundance of cuttings from each plant; self branching initiated at fully developed nodes 4"-5" above the soil line in 4" pots, with six to eight mature leaves, a unique characteristic, and the characteristic of controlling top growth and side bracts by properly managing side growth and primary foliage.

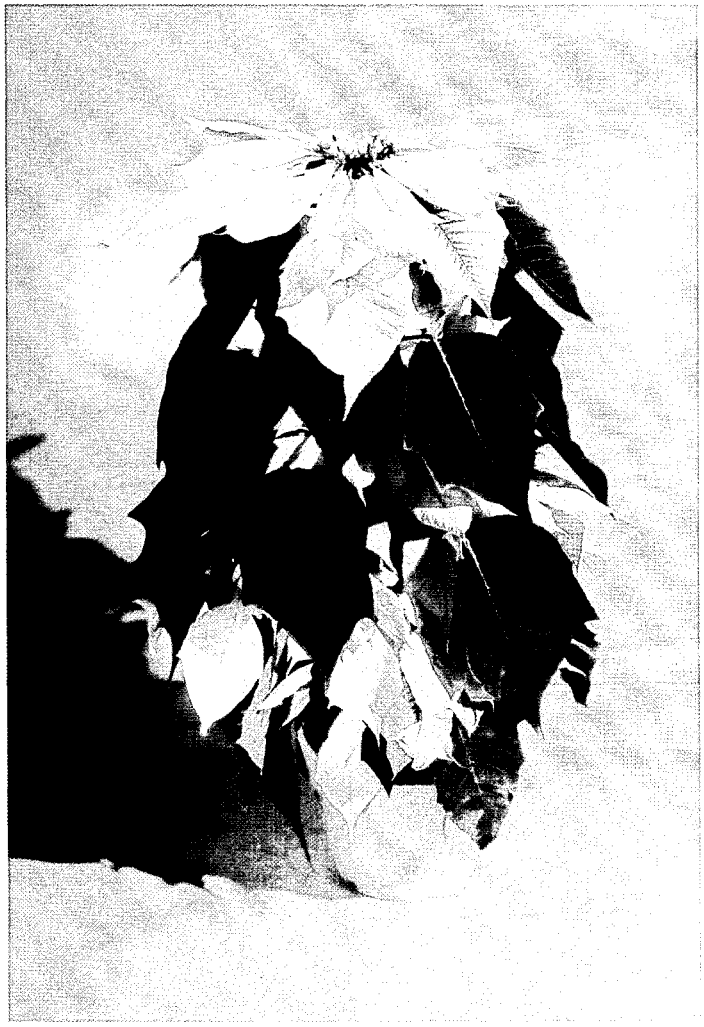

* * * * *